United States Patent
O'Dea et al.

(10) Patent No.: US 9,572,544 B2
(45) Date of Patent: Feb. 21, 2017

(54) DEPLOYABLE GUARD FOR MOBILE X-RAY SYSTEM

(71) Applicant: Carestream Health, Inc., Rochester, NY (US)

(72) Inventors: Dennis J. O'Dea, Farmington, NY (US); Craig F. Hofmann, Fairport, NY (US)

(73) Assignee: Carestream Health, Inc., Rochester, NY (US)

( * ) Notice: Subject to any disclaimer, the term of this patent is extended or adjusted under 35 U.S.C. 154(b) by 239 days.

(21) Appl. No.: 14/572,850

(22) Filed: Dec. 17, 2014

(65) Prior Publication Data
US 2016/0174915 A1    Jun. 23, 2016

(51) Int. Cl.
*A61B 6/10* (2006.01)
*A61B 6/00* (2006.01)
*A61B 6/02* (2006.01)
*A61B 6/06* (2006.01)

(52) U.S. Cl.
CPC .............. *A61B 6/547* (2013.01); *A61B 6/025* (2013.01); *A61B 6/06* (2013.01); *A61B 6/107* (2013.01); *A61B 6/4007* (2013.01); *A61B 6/4405* (2013.01); *A61B 6/467* (2013.01); *A61B 6/589* (2013.01); *A61B 6/487* (2013.01)

(58) Field of Classification Search
CPC .............. A61B 6/00; A61B 6/04; A61B 6/10; A61B 6/107; A61B 6/44; A61B 6/54; A61B 6/547; A61B 6/4405
USPC .................................................. 378/198, 204
See application file for complete search history.

(56) References Cited

U.S. PATENT DOCUMENTS

| | | | |
|---|---|---|---|
| 7,505,562 B2 | 3/2009 | Dinca et al. | |
| 8,172,633 B2 | 5/2012 | Park et al. | |
| 9,121,805 B2 * | 9/2015 | Omura ................. | A61B 6/4405 |
| 2011/0003109 A1 | 1/2011 | Slinker et al. | |

OTHER PUBLICATIONS

Je Hwang Ryu, et al., "Carbon Nanotube Electron Emitter for X-ray Imaging," Materials, 2012, 5, pp. 2353-2359.

* cited by examiner

*Primary Examiner* — Jurie Yun

(57) ABSTRACT

A boom has an x-ray head attached to one end thereof and the x-ray head has an x-ray source disposed therein. In a docked position of the boom, the x-ray source is disabled. In a deployed position, the x-ray source is enabled. A handle attached to the x-ray head is movable into at least two different positions. A first one of the positions disables the x-ray source while a second one of the positions enables the x-ray source. The handle extends a preselected distance from the x-ray source such that the handle maintains at least the preselected distance between the x-ray source and a subject to be exposed thereby.

16 Claims, 9 Drawing Sheets

DEPLOYABLE GUARD FOR MOBILE X-RAY SYSTEM

TECHNICAL FIELD

The disclosure relates generally to the field of mobile radiography and, more particularly, to apparatus and methods for providing a system configuration that allows ease of use and conformance to standards.

BACKGROUND

Mobile x-ray apparatus are of particular value in intensive care unit (ICU) and other environments where timely acquisition of a radiographic image is important. Because it can be wheeled around the ICU or other area and brought directly to the patient's bedside, a mobile x-ray apparatus allows an attending physician or clinician to have recent information on the condition of a patient and helps to reduce the risks entailed in moving patients to stationary equipment in the radiological facility.

As mobile x-ray systems have become more widely accepted and used, continued research and development has expanded their capabilities beyond those of single-image radiography, based on the x-ray film radiography model. By configuring mobile x-ray systems with an array of multiple, smaller x-ray sources, such as sources formed using carbon nanotube (CNT) technology, additional imaging modalities can be provided. This allows the mobile x-ray apparatus to provide not only conventional 2-D x-ray radiography images, but also to provide volume imaging using tomosynthesis or computed tomography (CT) methods, such as cone-beam computed tomography (CBCT), as well as fluoroscopy using multiple x-ray sources. To provide this expanded capability, the x-ray source can have a single x-ray emitter tube of conventional design, supplemented by multiple x-ray emitters, including an array of carbon nanotube (CNT) x-ray sources, for example.

In order to allow multiple modalities and maintain system portability, operational parameters such as positioning of the x-ray source(s) relative to the patient, dosage levels, operator procedure, and other factors must be readily changeable. This places some demanding requirements on design of support and positioning hardware for the x-ray head, requiring various guidance and guard elements that do not interfere with portability and smooth operation.

One concern for mobile x-ray equipment relates to maintaining sufficient distance between the x-ray source and the patient. If the patient is too close to the x-ray source, radiation levels can be excessive and image quality can be poor. International Electrotechnical Commission (IEC) standard IEC 60601-1 presents a number of general requirements for safety for medical electrical equipment. Among stipulations for compliance with IEC 60601-1, is the requirement for a physical barrier that is no less than about 30 cm from the x-ray source. This physical barrier forces the distance between the patient and the source to exceed at least about 30 cm for any of the imaging modalities available from the mobile x-ray system.

Thus, it can be appreciated that there are a number of considerations related to proper patient care, x-ray source positioning, and operational procedures for a mobile x-ray apparatus that provides multiple imaging modalities.

SUMMARY

It is an object of the present disclosure to advance the art of mobile radiography. A related object of the present disclosure is to address the need for features that help to configure a system that provides multiple imaging modalities, all while maintaining the portability of the mobile radiography system and conformance to standards.

These objects are given only by way of illustrative example, and such objects may be exemplary of one or more embodiments of the invention. Other desirable objectives and advantages inherently achieved by the may occur or become apparent to those skilled in the art. The invention is defined by the appended claims.

According to one aspect of the disclosure, a boom with an x-ray head is attached to one end thereof, the x-ray head having an x-ray source disposed therein and includes a docked position wherein the x-ray source in the tube head is disabled. The boom is undocked in a deployed position wherein the x-ray source in the tube head is energizable. A handle is attached to the tube head, wherein the handle is movable into at least two different positions with respect to the tube head, a first one of the positions disables the x-ray source, a second one of the positions enables activation of the x-ray source, and wherein the handle extends a preselected distance outward from the x-ray source when moved into the second position such that the handle maintains at least the preselected distance between the x-ray source and a subject to be exposed by the x-ray source.

This brief summary of the invention is intended only to provide a brief overview of subject matter disclosed herein according to one or more illustrative embodiments, and does not serve as a guide to interpreting the claims or to define or limit the scope of the invention, which is defined only by the appended claims. This brief summary is provided to introduce an illustrative selection of concepts in a simplified form that are further described below in the detailed description. This brief summary is not intended to identify key features or essential features of the claimed subject matter, nor is it intended to be used as an aid in determining the scope of the claimed subject matter. The claimed subject matter is not limited to implementations that solve any or all disadvantages noted in the background.

For example, the summary descriptions above are not meant to describe individual separate embodiments whose elements are not interchangeable. In fact, many of the elements described as related to a particular embodiment can be used together with, and possibly interchanged with, elements of other described embodiments. Many changes and modifications may be made within the scope of the present invention without departing from the spirit thereof, and the invention includes all such modifications. The drawings below are intended to be drawn neither to any precise scale with respect to relative size, angular relationship, relative position, or timing relationship, nor to any combinational relationship with respect to interchangeability, substitution, or representation of a required implementation.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE EMBODIMENTS

The following is a detailed description of the preferred embodiments, reference being made to the drawings in which the same reference numerals identify the same elements of structure in each of the several figures. Various relative terms such as "above," "below," "top," "bottom," "height," "depth," "width," and "length," etc. may be used in the present disclosure to facilitate description of various embodiments. The relative terms are defined with respect to a conventional orientation of a structure and do not necessarily represent an actual orientation of the structure in manufacture or use. The following detailed description is, therefore, not to be taken in a limiting sense.

Where they are used, the terms "first", "second", and so on, do not necessarily denote any ordinal or priority relation, but may be used for more clearly distinguishing one element or time interval from another. As used herein, the term "energizable" relates to a device or set of components that perform an indicated function upon receiving power and, optionally, upon receiving an enabling signal. The opposite state of "energizable" is "disabled". The term "actuable" has its conventional meaning, relating to a device or component that is capable of effecting an action in response to a stimulus, such as in response to an electrical signal, for example. The term "modality" is a term of art that refers to types of imaging. Modalities for an imaging system may be conventional x-ray, fluoroscopy or pulsed radiography, tomosynthesis, tomography, ultrasound, MMR, or other types of imaging. The term "subject" refers to the patient who is being imaged and, in optical terms, can be considered equivalent to the "object" of the corresponding imaging system. In the context of the present disclosure, the term "coupled" is intended to indicate a mechanical association, connection, relation, or linking, between two or more components, such that the disposition of one component affects the spatial disposition of a component to which it is coupled. For mechanical coupling, two components need not be in direct contact, but can be linked through one or more intermediary components or fields. It will be understood that when an element is referred to as being "connected," or "coupled," to another element, it can be directly connected or coupled to the other element or intervening elements or magnetic fields may be present. In contrast, when an element is referred to as being "directly connected," or "directly coupled," to another element, there are no intervening elements present. Other words used to describe the relationship between elements should be interpreted in a like fashion (e.g., "between" versus "directly between"; "adjacent" versus "directly adjacent"; etc.). The term "exemplary" indicates that the description is used as an example, rather than implying that it is an ideal.

Reference is made to the article by Je Hwang Ryu, Jung Su Kang, and Kyu Chang Park, entitled "Carbon Nanotube Electron Emitter for X-ray Imaging" in *Materials,* 2012, 5, 2353-2359; and to U.S. Pat. No. 8,172,633 to Park et al., filed Apr. 4, 2007; U.S. Patent Application Publication No. 2011/0003109 by Slinker et al., filed Jul. 1, 2009; U.S. Pat. No. 7,505,562 to Dinca et al., filed Apr. 19, 2007.

Figure 1:
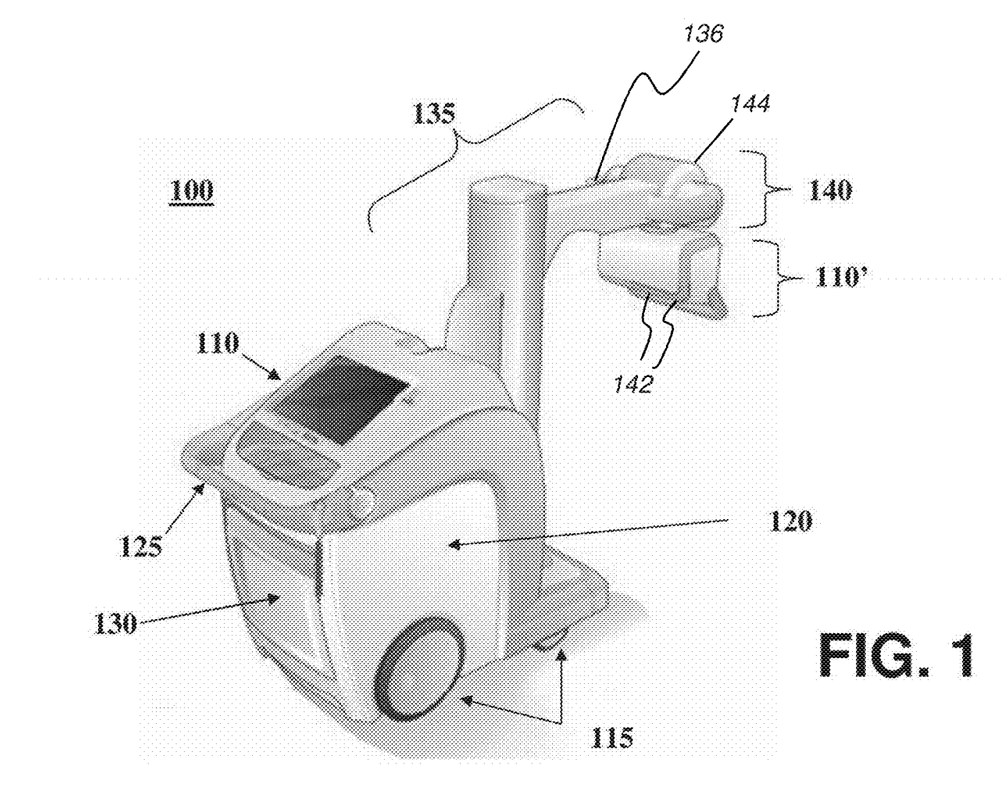
FIG. 1 is a diagram that shows a perspective view of a mobile radiography unit according to one embodiment of the application.

FIG. 1 is a diagram that shows a perspective view of a mobile radiography apparatus 100 that can use one or more portable radiographic detectors or flat panel detectors adapted to acquire digital image data according to radiation received from the x-ray sources according to embodiments of the application. The exemplary mobile x-ray or radiography apparatus 100 of FIG. 1 can be employed for a number of imaging modalities, including digital radiography (DR), tomosynthesis, fluoroscopy, and CT. As shown in FIG. 1, mobile radiography apparatus 100 can include a moveable transport frame 120 that includes a first display 110 and an optional second display 110' to display relevant information such as obtained images and related setup and operational data. An x-ray head 140 has a housing 144 mounted on a column assembly 135 and extending from a boom 136 that is part of column assembly 135. X-ray head 140 has one or more x-ray sources 142 for providing imaging in different modalities. As shown in FIG. 1, the second display 110' can be pivotably mounted adjacent to x-ray head 140 to be viewable or touchable in any angle of a 360 degree area.

The displays 110, 110' may provide user operated controls (e.g., touch screens) for initiating and directing functions such as generating, storing, transmitting, modifying, and printing of an obtained image(s) and may include an integral or separate control panel (not shown) to assist in implementing functions such as generating, storing, transmitting, modifying, and printing of an obtained image(s). Alternatively, one or more of displays 110, 110' can be separable from the apparatus 100 frame.

For mobility, the mobile radiographic apparatus 100 can have one or more wheels 115 and one or more handle grips 125, typically provided at waist-level, arm-level, or hand-level, that help an operator or technician to guide the mobile radiographic apparatus 100 to its intended location. A self-contained battery pack (e.g., rechargeable) can provide source power, which can reduce or eliminate the need for a power outlet near the area of operation. Further, the self-contained battery pack can provide for motorized transport.

For storage, the mobile radiographic apparatus 100 can include an area/holder for holding/storing one or more digital radiographic (DR) detectors or computed radiography cassettes. The area/holder can be storage area 130 (e.g., disposed on the frame 120) configured to removably retain at least one digital radiography (DR) detector. The storage area 130 can be configured to hold a plurality of detectors and can also be configured to hold one size or multiple sizes of DR detectors and/or batteries therein.

Mounted to frame 120 is a support column assembly 135 that supports one or more x-ray sources 142 of x-ray head 140 that can be mounted to the support column assembly 135 on extendable boom 136. In the embodiment shown in FIG. 1, the column assembly 135 can include a boom 136 that extends outward a fixed or variable distance from a vertical column section that may be configured to be extendible in a vertical direction to a desired height for obtaining a radiographic image. In addition, the supporting column assembly 135 may be rotatably attached to the moveable frame 120. According to one embodiment, the x-ray head 140 may be rotatably coupled to boom 136. In another exemplary embodiment, an articulated member of the support column that bends at a joint mechanism can allow movement of the x-ray head 140 over a range of vertical and horizontal positions. Height settings for the x-ray head 140 may range from low height for imaging of feet, ankles, and other lower extremities, to shoulder height and above for imaging the upper body portions of patients in various positions.

Figure 2:
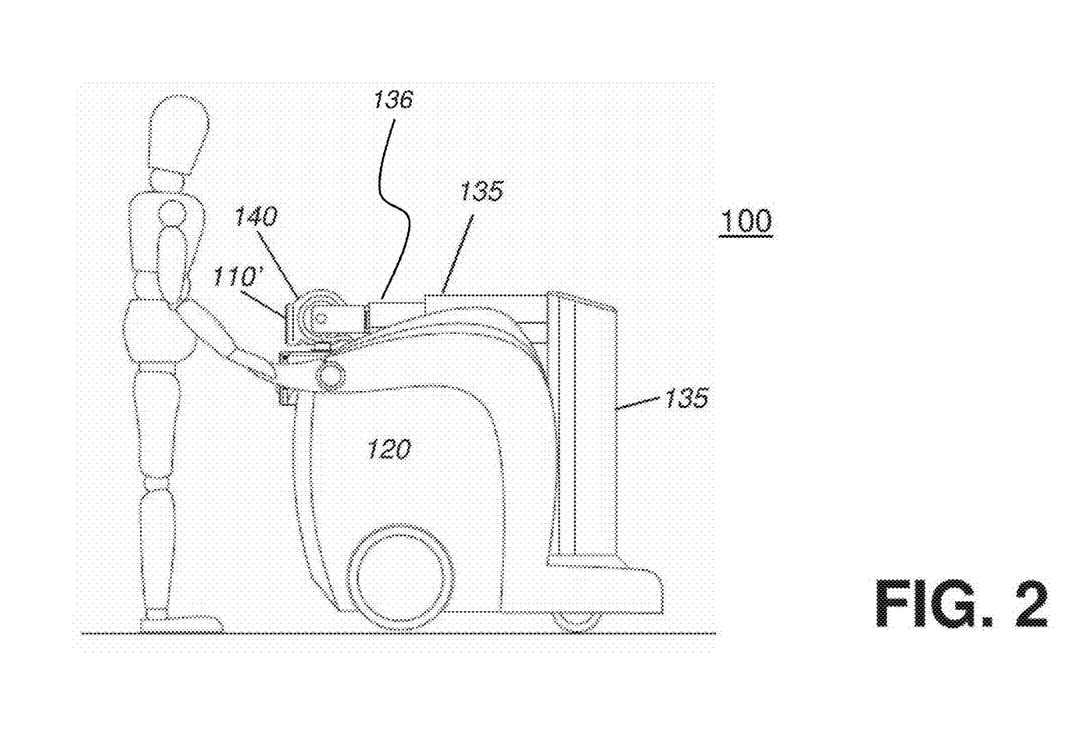
FIG. 2 is a diagram that shows a perspective view of a mobile radiography unit of FIG. 1 positioned for travel.

As shown in FIG. 2, for ease of transport of the mobile radiographic apparatus 100, column assembly 135 may be folded or retracted and x-ray head 140 may be positioned close to frame 120 in a docked configuration of the mobile radiographic apparatus 100. As shown in FIG. 2, the second display 110' can be in a viewable position (e.g., operable) while docked during transport of the mobile radiographic apparatus 100. When the mobile radiographic apparatus 100 is to be used, the column assembly 135, boom 136, and x-ray head 140 can be extended from the frame 120 for proper positioning (e.g., by the operator, a user, a practitioner, or x-ray technician) and the second display 110' moved to a viewable position such as shown in FIG. 1.

Figure 3:
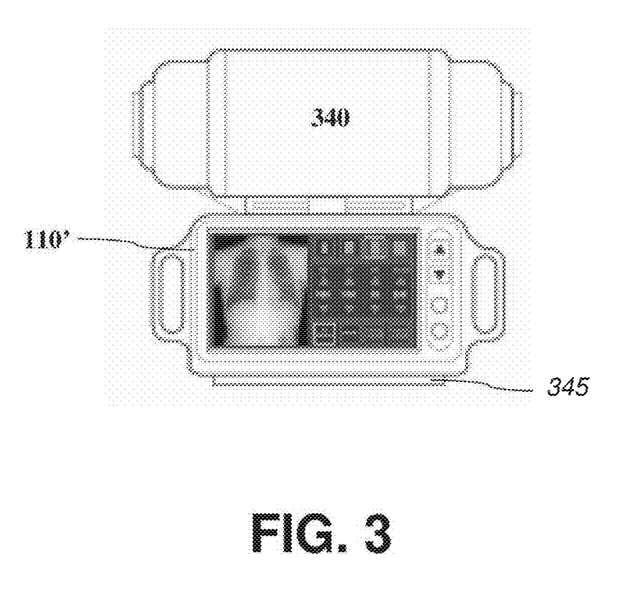
FIG. 3 is a diagram that shows an exemplary embodiment of a display/monitor as a second display mounted to a boom assembly of a mobile radiography unit according to the application.

FIG. 3 is a diagram that shows an exemplary embodiment of the display/monitor 110' used as a second display mounted to the boom 136 of the mobile radiographic apparatus 100 according to the present application. As shown in FIGS. 1-3, the second display 110' can be mounted to a collimator 345 of an x-ray source 340 of column assembly 135 of mobile radiography apparatus 100. In one embodiment, the collimator 345 can be rotatably mounted to the x-ray source 340 so that the collimator 345 (and second display 110') can swivel at least 90 degrees in one embodiment, at least 180 degrees in another embodiment, or 360 degrees plus. As shown in FIG. 3, the second display 110' is coupled to a plurality of handles for ease of positioning. Alternatively, the second display 110' may be rotatably mounted to an x-ray source 340 above the collimator 345 of the mobile radiographic apparatus 100.

The Applicants have recognized the need for an imaging apparatus that allows multiple positions of x-ray head 140 and allows the use of multiple x-ray emitters to allow different imaging modalities. Apparatus and methods of the present invention address the need for an interlocked handle arrangement that allows multiple x-ray head positions. The handle may be conveniently retracted against the x-ray head when the x-ray head is docked for ease of transport of the mobile radiographic apparatus 100.

Figure 4A:
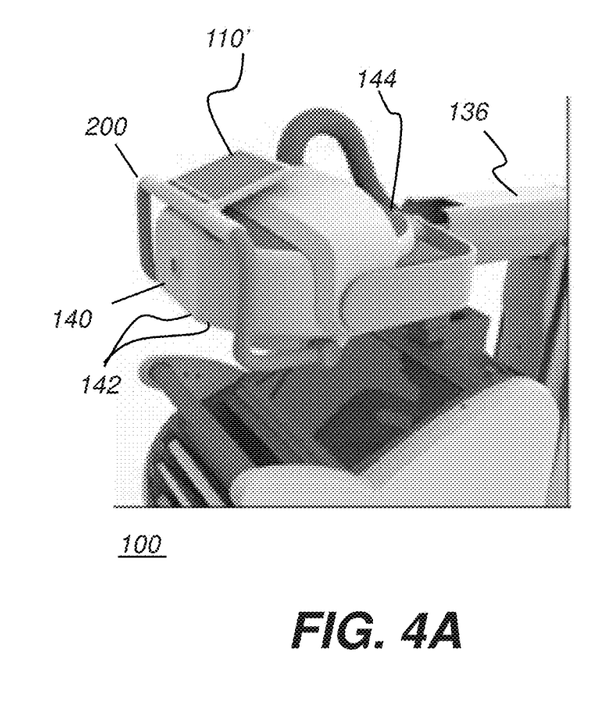
FIG. 4A shows a perspective view of a handle provided on the x-ray head and in a folded position for transport.
Figure 4B:
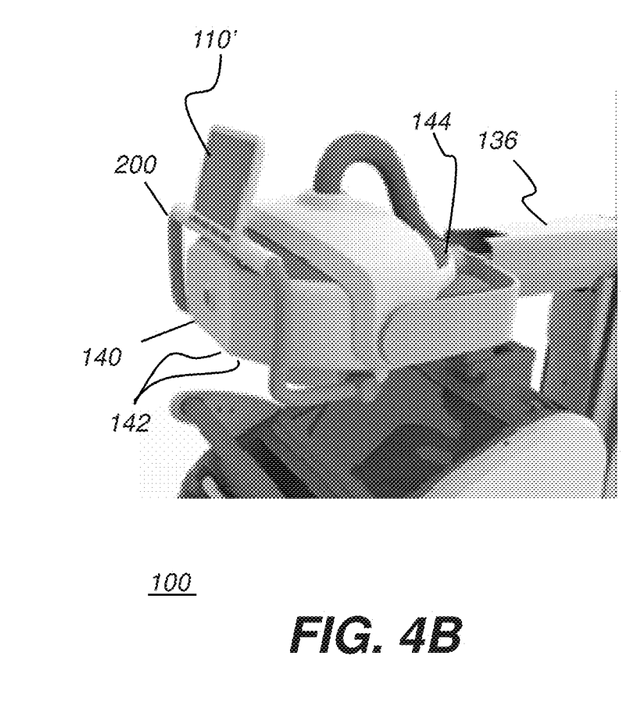
FIG. 4B shows a perspective view of a handle provided on the x-ray head and in a folded position for transport, with a display monitor tilted upward for viewing.

The perspective views of FIGS. 4A, 4B, 4C, and 4D show x-ray head 140 in different positions for transport, setup, and operation. FIG. 4A shows x-ray head 140 in a docked position. A handle 200 is in a first, folded position against x-ray head 140. Handle 200 may be coupled to the x-ray head housing 144 or to boom 136. X-ray head 140 may be automatically disabled while in a docked position using sensors that detect the x-ray head in the docked position. An interlock coupled to handle 200 (described subsequently) may act to prevent x-ray sources 142 in x-ray head 140 from being inadvertently energized with the handle 200 in the first position. In the docked position, display monitor 110' may be tilted fully back, as shown in FIG. 4A, in a transport position and may not be usable for x-ray control in this position; however, the monitor may be configured to remain active to enable control or other features not associated with x-ray imaging. The perspective view of FIG. 4B shows handle 200 in a folded, docked position but with display 110' tilted upward to allow viewing the display for obtaining status or for entering instructions.

According to an embodiment of the present disclosure, the handle 200 may be configured to be in the first position when the x-ray head is docked. The x-ray head 140 may be configured so that it will not properly fit or settle into docked position if the handle 200 is not folded.

Figure 4C:
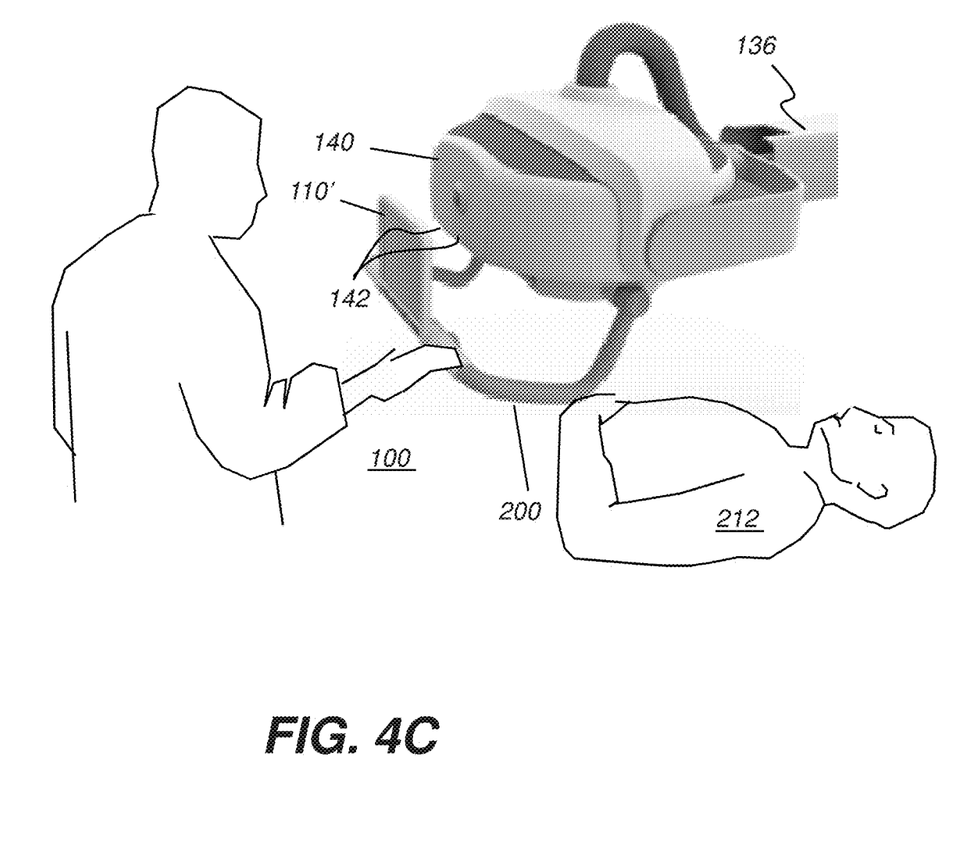
FIG. 4C shows a perspective view of a handle provided on the x-ray head and in an intermediate position for conventional 2-D radiography.

FIG. 4C shows x-ray head 140 in position for radiography imaging of a patient 212, such as at a height that brings the head 140 close to the patient 212. As shown, handle 200 may be lowered to a second, intermediate position. The x-ray sources can be energized with handle 200 at this intermediate position, as the interlock is not applied. Display 110' may be tilted to an appropriate angle for operator viewing. At this intermediate position, handle 200 is sized and configured to constrain proximity of the x-ray head 140 to the patient 212 so that the head 140 is no closer than a preselected distance from the patient 212, which distance is defined and limited by a size and configuration of the handle 200.

Figure 4D:
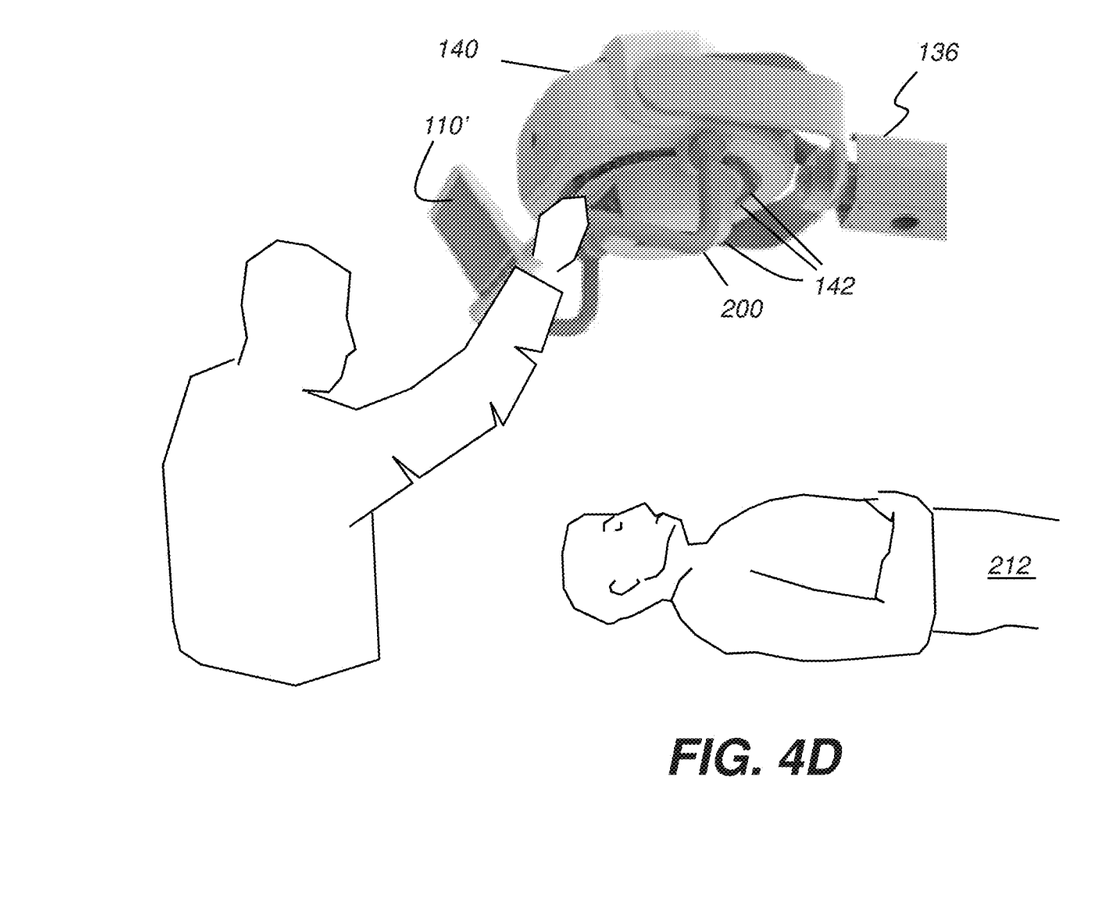
FIG. 4D shows a perspective view of a handle provided on the x-ray head and in a fully deployed position for tomosynthesis imaging.

FIG. 4D shows x-ray head 140 in position where it is energizable for tomosynthesis imaging of patient 212. For this modality, x-ray head 140 is placed at further distance from the patient 212 than in the FIG. 4C configuration. Multiple x-ray sources 142 may be used in a programmed sequence to obtain a set of images at suitable angles for capturing images that contain depth information pertaining to anatomical portions or regions of the patient 212. As shown in FIG. 4D, handle 200 is at a third, fully deployed position. Similar to the intermediate position of FIG. 4C, handle 200 constrains a distance or movement of x-ray head 140 so that the head 140 is no closer than a preselected minimum distance from patient 212. In FIGS. 4C and 4D, handle 200 extends a preselected distance forward of the x-ray source (e.g. downward in the view shown in these figures) when moved into the second or third position such that the handle maintains the preselected distance between the x-ray source and a subject to be exposed by the x-ray source.

The position of the handle 200 may be sensed or detected, such as by using a detente mechanism, for example, to enable or disable a corresponding imaging modality as an additional safety feature. When the handle 200 is in the position shown in FIG. 4C, the mobile radiography apparatus may be configured to automatically enable, under electronic control, conventional 2-D radiography, while a tomosynthesis capability may be automatically disabled. When the handle 200 is shifted by an operator into the position shown in FIG. 4D, the mobile radiography apparatus may be configured to automatically enable or activate a tomosynthesis imaging modality. When handle 200 is between the positions shown in FIGS. 4C and 4D, the mobile radiography apparatus may be configured to automatically disable or deactivate the x-ray source(s).

Figure 5A:
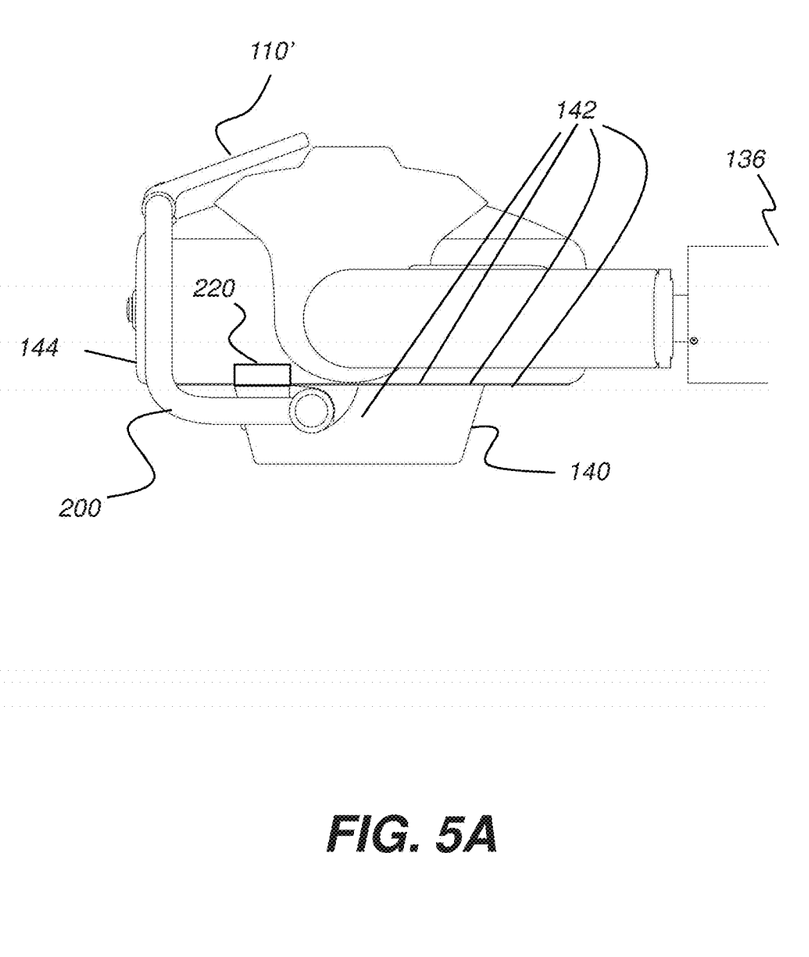
FIG. 5A is a side view that shows the handle in a folded position.
Figure 5B:
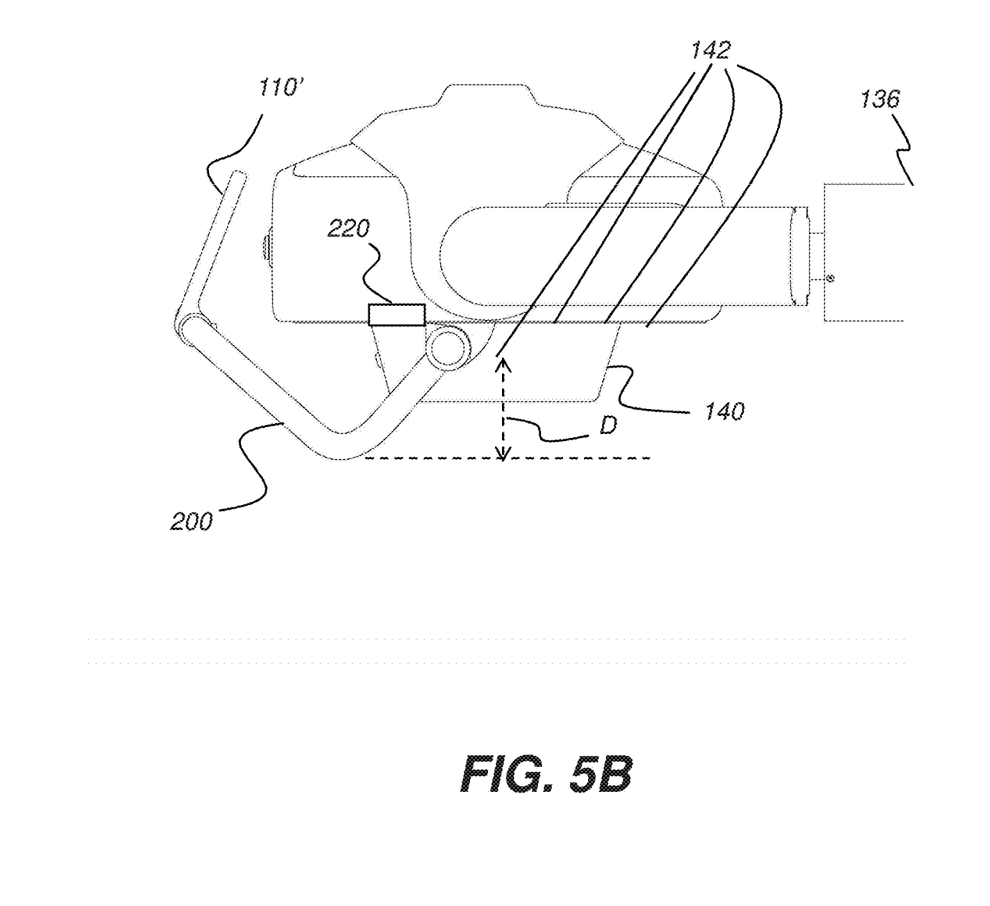
FIG. 5B is a side view that shows the handle in an intermediate position.
Figure 5C:
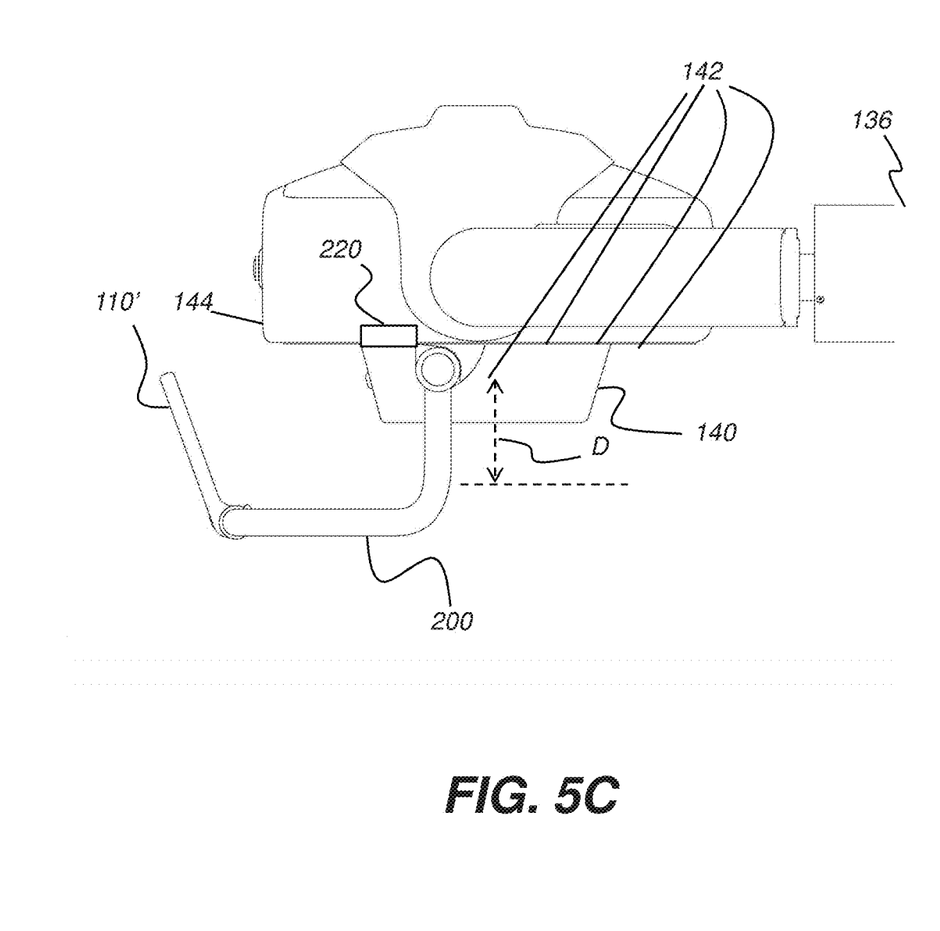
FIG. 5C is a side view that shows the handle in a fully deployed position.

FIG. 5A shows a side view of x-ray head 140 according to an embodiment of the present disclosure, with handle 200 in the docking or folded first position. FIG. 5B shows x-ray head 140 with handle 200 in the intermediate or second position. FIG. 5C shows x-ray head 140 with handle 200 in the fully deployed or third position. X-ray head in FIGS. 5A-5C has a number of emissive x-ray sources 142 for conventional radiography as well as for tomosynthesis and fluoroscopy applications.

FIGS. 5B and 5C show a distance D that represents a preselected minimum separation distance between radiation sources 142 and the patient. As can be seen from FIG. 5B, the intermediate position of handle 200 as it extends from housing 144 provides a physical barrier, between the source 142 and the patient, sized and configured appropriately for standards such as IEC 60601-1 as described herein. The fully deployed position of the handle 200 as shown in FIG. 5C also provides this minimum separation barrier and at least the same distance D as shown in FIG. 5B. A sensor 220, such as a switch or Hall Effect sensor, for example, may provide an electric output signal to the mobile radiography apparatus 100 indicative of the position of the handle 200 as detected by the sensor 220. This output signal may be an interlock signal initiating the mobile radiography apparatus 100 to disable or deactivate x-ray sources 142 when handle 200 is not in an appropriate position. Thus, for example, sensor 220 would provide a first signal or signal condition that indicates handle 200 is in the folded first position. A second signal or signal condition would indicate that handle 200 is either in the intermediate second position of FIG. 5B or in the fully deployed third position of FIG. 5C. The same signal could be generated and transmitted to indicate both intermediate and fully deployed positions. Alternatively, each of the three positions of the handle 200 may be configured to cause a different type of signal, or different data in the signal, to be generated and transmitted. Control logic in the mobile radiography apparatus 100 may be programmably configured to energize the x-ray sources 142 for a corresponding imaging modality in response to the type of signal, or signal data, received. Alternatively, the sensor 220 may output a signal that indicates that handle 200 is moving or disposed between defined positions.

When the handle 200 is in the folded first position, the tube head display 110' may be disposed in a convenient viewing position. Also, the fully deployed position of FIG. 5C extends the handle 200 downward to help reduce the reach distance needed by an operator during set up of a tomosynthesis imaging modality that may require a longer source-to-image distance (SID).

The invention has been described in detail, and may have been described with particular reference to a suitable or presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed is:

1. A boom comprising an x-ray head attached to one end thereof, the x-ray head having an x-ray source disposed therein, the x-ray head comprising:
   a docked position wherein the x-ray source in the x-ray head is disabled and the boom is docked;
   a deployed position wherein the x-ray source in the x-ray head is energizable and the boom is undocked; and
   a handle attached to the x-ray head, wherein the handle is movable into at least two different positions with respect to the x-ray head, a first one of the positions disables the x-ray source, a second one of the positions enables activation of the x-ray source, and wherein the handle extends a preselected distance outward from the x-ray source when moved into the second position such that the handle maintains at least the preselected distance between the x-ray source and a subject to be exposed by the x-ray source.

2. The boom of claim 1 wherein the preselected distance is at least about 30 centimeters.

3. The boom of claim 1 wherein the x-ray head further comprises a tiltable display monitor coupled to the handle, the monitor configured to remain active while the handle is placed into the first position and the x-ray head is docked.

4. The boom of claim 1 wherein the handle is configured to be in the first position when the x-ray head is docked.

5. The boom of claim 1 wherein the handle is movable into a third position that enables energization of the x-ray source, and wherein the third position is such that the handle maintains at least the preselected distance between the x-ray source and the subject to be exposed by the x-ray source.

6. The boom of claim 5 wherein at least a portion of the handle extends outward further than the first or second position when the handle is in the third position.

7. The boom of claim 5 wherein the x-ray source is disabled when the handle is between the second and third positions.

8. The boom of claim 1 further comprising a sensor that provides an output signal indicative of the position of the handle.

9. The boom of claim 8 wherein the sensor is a Hall effect sensor.

10. A mobile radiography apparatus comprising:
    a column with an extendable boom;
    an x-ray head coupled to the extendable boom, wherein the x-ray head has a housing and at least one x-ray source;
    a handle coupled to the housing or extendable boom, wherein the handle is extended outward from the x-ray head, wherein the handle has a first position folded against the housing and at least a second position extending outward from the housing by at least a predetermined distance,
    wherein the handle maintains at least a preselected distance between the x-ray source and a subject to be exposed by the x-ray source; and
    a sensor that provides a signal that is indicative of the position of the handle.

11. The apparatus of claim 10 wherein the sensor is a Hall effect sensor.

12. The apparatus of claim 10 wherein the x-ray head has a plurality of carbon nanotube x-ray emitters.

13. The apparatus of claim 10 wherein the handle further has a third position extending outward from the housing and wherein the second position is used for a first imaging modality and the third position is used for a second imaging modality.

14. The apparatus of claim 10 further comprising a display monitor coupled to the handle.

15. The apparatus of claim 14 wherein the display monitor is tiltable about the handle.

16. The apparatus of claim 10 wherein the preselected distance is at least about 30 centimeters.

\* \* \* \* \*

UNITED STATES PATENT AND TRADEMARK OFFICE
CERTIFICATE OF CORRECTION

PATENT NO. : 9,572,544 B2  Page 1 of 1
APPLICATION NO. : 14/572850
DATED : February 21, 2017
INVENTOR(S) : Dennis J. O'Dea et al.

It is certified that error appears in the above-identified patent and that said Letters Patent is hereby corrected as shown below:

In the Claims

Column 8, Claim 7, Line 30 Replace the number "5" with the number --1--

Column 8, Claim 8, Line 33 Replace the number "1" with the number --7--

Column 8, Claim 9, Line 36 Replace the number "8" with the number --5--

Signed and Sealed this
Seventh Day of November, 2017

Joseph Matal
*Performing the Functions and Duties of the*
*Under Secretary of Commerce for Intellectual Property and*
*Director of the United States Patent and Trademark Office*